United States Patent [19]

Leong

[11] 4,341,844

[45] Jul. 27, 1982

[54] ARTICLE HAVING ORGANO-PHOSPHONITRILE RUBBER COATING BONDED TO NATURAL OR SYNTHETIC RUBBER AND METHOD OF MAKING

[75] Inventor: Koon-Wah Leong, Schaumberg, Ill.

[73] Assignee: The Kendall Company, Boston, Mass.

[21] Appl. No.: 253,298

[22] Filed: Apr. 13, 1981

Related U.S. Application Data

[60] Division of Ser. No. 88,157, Oct. 25, 1979, Pat. No. 4,311,736, which is a continuation-in-part of Ser. No. 21,336, Mar. 19, 1979, abandoned.

[51] Int. Cl.³ .................. B32B 25/08; A61F 7/12; B32B 27/08

[52] U.S. Cl. .................. 428/492; 128/349 R; 427/331; 427/372.2; 428/447; 428/451; 428/494; 428/495; 428/521; 428/522

[58] Field of Search .............. 428/494, 492, 495, 451, 428/447, 521, 522; 528/399, 401; 128/349 R; 427/331, 372.2

[56] References Cited

U.S. PATENT DOCUMENTS

| | | | |
|---|---|---|---|
| 3,340,088 | 9/1967 | Pennisi et al. | 428/494 X |
| 3,515,688 | 6/1970 | Rose | 528/399 |
| 3,888,799 | 6/1975 | Rose et al. | 528/401 X |
| 3,940,547 | 2/1976 | Needham et al. | 428/494 X |

Primary Examiner—Thomas J. Herbert, Jr.

[57] ABSTRACT

A coating of organo-phosphonitrile polymer is bonded to the surface of a cured rubber article such as a catheter with a primer coating containing a cross-linked di- or poly-vinyl compound.

5 Claims, No Drawings

ARTICLE HAVING ORGANO-PHOSPHONITRILE RUBBER COATING BONDED TO NATURAL OR SYNTHETIC RUBBER AND METHOD OF MAKING

This is a division of application Ser. No. 88,157 filed Oct. 25, 1979, now U.S. Pat. No. 4,311,736 which is in turn a continuation-in-part of application Ser. No. 21,336 filed Mar. 19, 1979, now abandoned.

This invention relates to a method of providing natural or synthetic rubber articles, particularly biomedical articles such as catheters, with a cured coating comprising a cured organo-phosphonitrile elastomeric polymer bonded to the surface of the articles, and to the articles so produced.

A variety of articles made of natural or synthetic rubber including silicone elastomer and butadiene-styrene rubber have desirable properties of strength and elasticity but have surface properties which are in some respects undesirable. This is particularly true in the case of biomedical devices made of natural rubber coming into contact with tissue and with body fluids such as urine or blood, as in the case of a variety of implants and particularly catheters made of natural or synthetic rubbers or elastomers such as embolectomy catheters and urinary catheters, e.g., Foley retention catheters. Although organo-phosphonitrile elastomeric polymers have been found to possess superior surface characteristics such as blood compatibility rendering them particularly useful in biomedical devices, the the high cost of such polymers has militated against their use for such devices. While coatings, including cured or cross-linked coatings of such polymers on natural or synthetic rubber devices have previously been proposed, the coatings have lacked adequate adhesion to the cured or vulcanized natural or synthetic rubber substrate, particularly when exposed to aqueous liquids such as blood or urine or other body fluids.

It has now been found that a coating comprising a cured organo-phosphonitrile elastomeric polymer can be bonded to the surface of an article of cured natural or other synthetic rubber by interposing a layer or primer coating which comprises a di- or poly-vinyl compound in the form of a hydrocarbon monomer or oligomer containing a plurality of vinyl groups cured or cross-linked in situ.

The organo-phosphonitrile elastomeric polymers which may be employed in the present invention are those generally linear polymers containing randomly distributed repeating units having the structures:

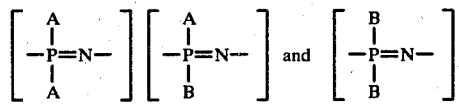

wherein A represents RO—, RNH—, $X(CF_2)O$—, or $X(CF_2)_m CH_2NH$—and B represents R'O—, R'NH, $Y(CF_2)_n CH_2O$—, or $Y(CF_2)_n CH_2NH$—, R and R' each being selected from the group consisting of lower alkyl and aryl such as phenyl, tolyl, chlorophenyl, X and Y each being selected from the group consisting of hydrogen and fluorine, and m and n each being an integer from 1 to 8 inclusive. Particularly useful in the present invention are elastomeric polymers having the foregoing composition in which A and B are not identical to each other but differ in one or more respects within the limits of the definition and in which A represents $X(CF_2)_m CH_2O$—and B represents $Y(CF_2)_n CH_2O$—.

The finished product is in the form of an article having a surface of cured or vulcanized natural or synthetic rubber, such as a catheter, having a primer coating on it surface comprising a cross-linked di- or poly-vinyl compound, and an outer coating comprising a cured organo-phosphonitrile polymer, the outer coating being bonded to said article by the primer coating.

Any of the usual synthetic rubbers may form the surface of the article, such as the rubbery polymers of isoprene or butadiene and rubbery copolymers of either of them with comonomers having an ethylenic unsaturation such as styrene, acrylonitrile, isobutylene, or the like, and rubbery ethylene-propylene-butadiene copolymers.

The outer coating composition, which is preferably in the form of a solution of the desired organo-phosphonitrile polymer in a suitable organic solvent such as a ketone, e.g., methyl ethyl ketone, methyl isobutyl ketone, tetrahydrofuran, ethyl trifluoroacetate, dimethyl formamide, or a liquid fluorocarbon, also contains a suitable curing or cross-linking agent such as an organic peroxide, e.g., benzoyl peroxide, acetyl peroxide, lauroyl peroxide, or mixtures of any two or more of these, in an amount from 0.1 to 5% by weight of the polymer. Any conventional accelerator such as magnesium oxide can be used along with the peroxide. There is also employed in the polymer as accelerator or co-curing agent an alkyl aluminum compound having the composition $$Al\ R_1R_2R_3$$

wherein $R_1$ is selected from the group consisting of hydrogen and alkyl having from 2 to 8 carbon atoms and $R_2$ and $R_3$ are alkyl having from 2 to 8 carbon atoms. Suitable alkyl aluminum compounds include diisobutyl aluminum hydride, triethyl aluminum, diisobutyl monoethyl aluminum, triisobutyl aluminum, and tri-n-octyl aluminum, as well as mixtures of any two or more of these. Amounts of alkyl aluminum compounds from 0.01 to 2% by weight of the polymer can be used. Coating compositions containing such alkyl aluminum compounds as accelerating or co-curing agents along with an organic peroxide cure to insoluble tough materials rapidly at room temperature, although higher temperatures up to 70° C., preferably 40°–70° C., can be used. By limiting the curing temperature to one no higher than 70° C., the outer coating composition can be applied to the surface of a previously vulcanized or cured natural or synthetic rubber article and cured satisfactorily without danger of overcuring or causing deterioration of the underlying rubber article. The peroxide curing agent can be dissolved in the same solvent as the polymer, but the alkyl aluminum compound used as accelerator is most readily available in the form of a solution in a hydrocarbon such as hexane or octane; such solution can simply be mixed with the solution of polymer and peroxide.

The organo-phosphonitrile polymer coating composition in the form of a solution in organic solvent can vary in concentration over a wide range, those containing from 2 to 20% of polymer based on the weight of solvent, depending on the viscosity which is desired or convenient, being the most useful.

The primer or bonding coating which must be first applied to the surface of the natural or synthetic rubber article before the organo-phosphonitrile polymer coating in order to provide bonding or adhesion of the latter to the natural or synthetic rubber comprises a priming agent which before cross-linking is in the form of a di- or poly-vinyl compound such as a hydrocarbon monomer or low molecular weight polymer containing a plurality of, i.e., two or more, polymerizable vinyl groups, together with an organic peroxide such as any of those used as curing agent for the curing of the organo-phosphonitrile polymer as described above. Among suitable hydrocarbon monomers and low molecular weight polymer priming agents are those having the structures:

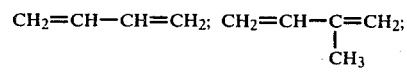

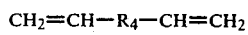

in which $R_4$ is aliphatic hydrocarbon containing 1 to 4 carbon atoms or aromatic hydrocarbon, e.g., phenylene; and low molecular weight polymers of these monomers in which the degree of polymerization is up to 100 and which contain two or more polymerizable vinyl groups, including those having the structure:

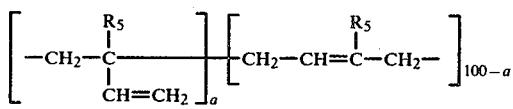

wherein $R_5$ is hydrogen or methyl and a is an integer from 2 to 100. Suitable priming agents include such monomers as 1,3-butadiene, isoprene, divinyl benzene, and low molecular weight polymers of these and similar monomers in which the degree of polymerization is up to 100 and which contain two or more polymerizable vinyl groups.

The primer or bonding coating is preferably applied to the surface of a natural or synthetic rubber article in the form of a solution; there may be used as solvent any of the ketone or other solvents used for the organo-phosphonitrile polymer; the amount of monomer or low molecular weight polymer primer or bonding agent in the coating preferably is from 0.01 to 2% by weight of the solvent.

The amount of organic peroxide cross-linking agent in the primer coating also can vary over a wide range, preferably from 10 to 150% by weight of the priming agent.

The following specific examples are intended to illustrate more fully the nature of the invention without acting as a limitation upon its scope.

EXAMPLES

Eight urinary catheters (12 Fr.) made of natural rubber latex were washed successively with distilled water, methanol, hexane, and methyl ethyl ketone and dried at room temperature for one hour. The surfaces of the catheters were treated with a priming solution for twenty minutes. The priming solution contained 0.04% divinyl benzene together with an equal weight of benzoyl peroxide, both dissolved in methyl ethyl ketone. After re-drying at room temperature for half an hour, the catheters were divided into two groups. One group was dipped in a coating solution prepared as described in the following paragraph.

There was employed an elastomeric fluoroalkoxy phosphonitrilic copolymer supplied by Firestone Tire and Rubber Company under the trade name PNF 200 having the composition set forth in U.S. Pat. No. 3,515,688 and having randomly distributed repeating units having the structures defined above. A 1.5 g specimen of this copolymer was dissolved in 37.5 ml methyl ethyl ketone (MEK). To this vigorously stirred copolymer solution, 0.50 ml α,α'-bis (t-butyl peroxy) diisopropyl benzene (Vulcup R) solution (0.75 g Vulcup R in 5.00 ml MEK) was added followed by 1.1 ml of a triisobutyl aluminum solution prepared by diluting 0.60 ml of a 25% by weight solution of triisobutyl aluminum in hexane to a total volume of 10.0 ml with MEK. The catheters were allowed to dry at room temperature for 15 minutes, after which the dipping and drying steps were repeated. The catheters were then heated at 60° C. for 15 hours to produce a clear and uniform cured coating which was firmly attached to the catheter surface and which exhibited no peeling or separation from the catheter surface after the catheter was repeatedly stretched and allowed to retract, as well as after it was immersed in distilled water for 24 hours. The coated catheters displayed tissue-reaction properties very similar to those of silicone catheters whereas the uncoated natural rubber catheters were found to be very cytotoxic. Because of the low temperature at which the cure or cross-linking of the copolymer coating is carried out, there is no appreciable change in the extent of cure of the previously cured natural rubber catheters. The coatings may vary in thickness over any desired range, being controlled by the concentration of the solution and the number of dips.

The second group of catheters was dipped in a coating solution prepared as described in the following paragraph.

The coating solution was the same as described above except that there was used, instead of the Vulcup R solution, 0.50 ml benzoyl peroxide solution (0.75 g benzoyl peroxide in 5.00 ml MEK).

The coated catheters were dried, recoated, and heated to cure as described above, and the finished catheters displayed essentially the same properties and characteristics as those described above.

Essentially the same results were obtained by substituting for the solution of divinyl benzene used as the primer a solution containing 0.04% by weight of a low molecular weight polymer of 1,3-butadiene (degree of polymerization about 55; m.w. about 3000) together with an equal weight of benzoyl peroxide in methyl ethyl ketone.

What is claimed is:

1. A cured article of natural or synthetic rubber having on its surface a primer coating comprising a cross-linked di- or poly-vinyl compound, and an outer coating comprising a cured organo-phosphonitrile polymer containing randomly distributed repeating units having the structures:

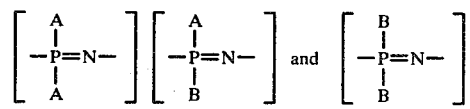

wherein A represents RO—, RNH—, X(CF$_2$)$_m$CH$_2$O—, or X(CF$_2$)$_m$CH$_2$NH—and B represents R'O, R'NH, Y(CF$_2$)$_n$CH$_2$O—, or Y(CF$_2$)$_n$CH$_2$NH—, R and R' each being selected from the group consisting of lower alkyl and aryl such phenyl, tolyl, chlorophenyl, X and Y each being selected from the group consisting of hydrogen and fluorine, and m and n each being an integer from 1 to 8 inclusive, said outer coating being bonded to said article by said primer coating.

2. A cured article as claimed in claim 1 which is a catheter.

3. A cured article as claimed in claim 1 in which said article is a catheter in which said organo-phosphonitrile polymer is one in which A represents X(CF$_2$)$_m$CH$_2$O— and B represents Y(CF$_2$)$_n$CH$_2$O—, X and Y each being selected from the group consisting of hydrogen and fluorine, and m and n each being an integer from 1 to 8.

4. A cured article as claimed in claim 3 in which said primer coating comprises cross-linked divinyl benzene.

5. A cured article as claimed in claim 3 in which said primer coating comprises cross-linked low molecular weight polymers of monomers having before cross-linking the structure:

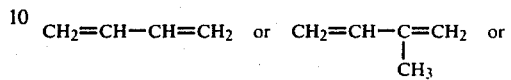

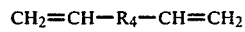

in which R$_4$ is aliphatic hydrocarbon containing 1 to 4 carbon atoms or aromatic hydrocarbon, said polymers having a degree of polymerization up to 100 and containing two or more polymerizable vinyl groups.

* * * * *